(12) United States Patent
Spuck

(10) Patent No.: US 11,786,407 B2
(45) Date of Patent: Oct. 17, 2023

(54) DYNAMIC VISION ENABLING VISOR

(71) Applicant: Associated Universities, Inc., Washington, DC (US)

(72) Inventor: Timothy Steven Spuck, Shippenville, PA (US)

(73) Assignee: Associated Universities, Inc., Washington, DC (US)

(*) Notice: Subject to any disclaimer, the term of this patent is extended or adjusted under 35 U.S.C. 154(b) by 471 days.

(21) Appl. No.: 16/896,374

(22) Filed: Jun. 9, 2020

(65) Prior Publication Data
US 2021/0038433 A1    Feb. 11, 2021

Related U.S. Application Data

(60) Provisional application No. 62/884,947, filed on Aug. 9, 2019.

(51) Int. Cl.
*A61F 9/08* (2006.01)

(52) U.S. Cl.
CPC .......... *A61F 9/08* (2013.01); *A61H 2201/165* (2013.01); *A61H 2201/5048* (2013.01); *A61H 2201/5064* (2013.01)

(58) Field of Classification Search
CPC .............. A61F 9/08; A61H 2201/1604; A61H 2201/165; A61H 2201/5048; A61H 2201/5064; A61H 3/061
See application file for complete search history.

(56) References Cited

U.S. PATENT DOCUMENTS

| | | | |
|---|---|---|---|
| 3,907,434 A | 9/1975 | Coles | |
| 4,712,003 A | 12/1987 | Ban et al. | |
| 5,097,326 A | 3/1992 | Meijer | |
| 5,487,669 A | 1/1996 | Kelk | |
| 2007/0211947 A1 | 9/2007 | Tkacik | |
| 2010/0149341 A1* | 6/2010 | Marks | A63F 13/40 348/169 |
| 2012/0053826 A1* | 3/2012 | Slamka | G01S 15/93 701/301 |
| 2013/0039152 A1* | 2/2013 | Liu | A61F 9/08 367/99 |
| 2015/0323325 A1 | 11/2015 | Caporizzo | |
| 2019/0282432 A1* | 9/2019 | Enenkel | G01S 7/51 |
| 2020/0286289 A1* | 9/2020 | Mitchell | G01C 15/002 |

FOREIGN PATENT DOCUMENTS

WO    WO2003032889    4/2003

OTHER PUBLICATIONS

PCT Search Report and Written Opinion for PCT/US20/36739, dated Mar. 4, 2021.

* cited by examiner

*Primary Examiner* — Kathleen V Nguyen
(74) *Attorney, Agent, or Firm* — Remenick PLLC

(57) ABSTRACT

Systems of presenting environmental data include a frequency emitting device, a frequency receiving device, wherein the frequency receiving device is tuned to receive a reflected signal from the frequency emitting device, a processor, and a sound emitting device adapted to play a sound transmission. The processor is programmed to compile data from the reflected signal and convert the data from the reflected signal into a sound transmission.

22 Claims, 3 Drawing Sheets

DYNAMIC VISION ENABLING VISOR

REFERENCE TO RELATED APPLICATIONS

This application claims priority to U.S. Provisional Application No. 62/884,947, filed Aug. 9, 2019, entitled "DYNAMIC VISION ENABLING VISOR," and hereby specifically and entirely incorporated by reference.

RIGHTS IN THE INVENTION

This invention was made with government support under NSF #1640131, between the National Science Foundation and Associated Universities, Inc., and, accordingly, the United States government has certain rights in this invention.

BACKGROUND

1. Field of the Invention

The invention is directed to systems and methods for transmitting information by sound, more specifically, the invention is directed to systems and methods of obtaining distance information and converting the information into an audible output.

2. Background of the Invention

Visual impairment, also known as vision impairment or vision loss, is a decreased ability to see to a degree that causes problems not fixable by usual means, such as glasses. The term blindness is used for complete or nearly complete vision loss. Visual impairment may cause people difficulties with normal daily activities such as driving, reading, socializing, and walking.

Many people with serious visual impairments can travel independently, using a wide range of tools and techniques. Some existing tools include canes, guide dogs, GPS devices, and echolocation. Sound is one of the most important senses that the blind or visually impaired use in order to locate objects in their surroundings. A form of echolocation is used, similarly to that of a bat. Echolocation from a person's perspective is when the person uses sound waves generated from speech or other forms of noise such as cane tapping, which reflect off of objects and bounce back at the person giving them a rough idea of where the object is. This does not mean they can depict details based on sound but rather where objects are in order to interact, or avoid them. Increases in atmospheric pressure and humidity increase a person's ability to use sound to their advantage as wind or any form of background noise impairs it.

A number of human studies show that blind persons perform nonvisual tasks better than those with sight. Neuroimaging studies of blind persons performing nonvisual tasks, including hearing, show activity in brain areas normally associated with vision. Many blind people have better pitch perception than sighted people. They also have better sound localization for sounds on the periphery of a space, and parts of the visual cortex are recruited for auditory sound processing in people who are blind. When a sound is in the horizontal plane (in front, behind or to either side) it is usually pinpointed binaurally—a brain compares the difference in sound timing between right and left ears. But when identifying sounds in the vertical plane (above or below, in a straight line from the top of a head), the sound travels an equal distance to each ear, so there are not right-left cues to give location information.

Therefore, there is a need for a device that can provide blind or visually impaired people more information about their surroundings in order to help them navigate the world.

SUMMARY OF THE INVENTION

The present invention overcomes the problems and disadvantages associated with current strategies and designs and provides devices and methods of providing distance information to users.

One embodiment of the invention is directed to a system of presenting environmental data. The system comprises a frequency emitting device, a frequency receiving device, wherein the frequency receiving device is tuned to receive a reflected signal from the frequency emitting device, a processor, and a sound emitting device adapted to play a sound transmission. The processor is programmed to compile data from the reflected signal and convert the data from the reflected signal into a sound transmission.

In a preferred embodiment, the frequency emitting device emits a plurality of signals directed toward at least a portion of the environment, the frequency receiving device is adapted to receive reflections from the plurality of signals, and the processor is adapted to differentiate between each sent and received signal and compile an array of data based on the received signals. Preferably, the processor converts the array of data into a sonification of the environment. The sonification of the environment is preferably a three-dimensional representation of the environment. Preferably, a tone of the sonification represents the horizontal position of a reflected signal, a volume of the sonification indicates a property of the reflected signal, and a time of the sonification represents a vertical position of the reflected signal. Preferably, the property is at least one of distance information, color information, density information, or combinations thereof.

Preferably, the frequency emitting device and the frequency receiving device is one of a LIDAR system, a RADAR system, or a SONAR system. At least a portion of the system is preferably wearable. Preferably, the frequency emitting device and the frequency receiving device continuously sweep the environment to update the data compiled by the processor and the sound transmission. Preferably, the sound emitting device continuously emits the sound transmission as the processor updates the sound transmission.

Another embodiment of the invention is directed to a method of presenting environmental data. The method includes the steps of emitting at least one frequency from a frequency emitting device, receiving a reflection of the at least one emitted frequency on a frequency receiving device, compiling data from the reflected signal on a processor, converting the data from the reflected signal into a sound transmission on the processor, and playing the sound transmission on a sound emitting device.

Preferably, the frequency emitting device emits a plurality of signals directed toward at least a portion of the environment, the frequency receiving device is adapted to receive reflections from the plurality of signals, and the processor is adapted to differentiate between each sent and received signal and compile an array of data based on the received signals. The method preferably further comprises converting the array of data into a sonification of the environment on the processor. In a preferred embodiment, the sonification of the environment is a three-dimensional representation of the environment. Preferably, a tone of the sonification represents the horizontal position of a reflected signal, a volume of the sonification indicates a property of the reflected signal, and a time of the sonification represents a vertical position of the reflected signal. Preferably, the property is at least one of distance information, color information, density information, or combinations thereof.

In a preferred embodiment, the frequency emitting device and the frequency receiving device is one of a LIDAR system, a RADAR system, or a SONAR system. Preferably, the frequency emitting device and the frequency receiving device continuously sweep the environment to update the data compiled by the processor and the sound transmission. The sound emitting device preferably continuously emits the sound transmission as the processor updates the sound transmission. The method preferably further comprises detecting a direction of a field of view.

Other embodiments and advantages of the invention are set forth in part in the description, which follows, and in part, may be obvious from this description, or may be learned from the practice of the invention.

DESCRIPTION OF THE DRAWING

The invention is described in greater detail by way of example only and with reference to the attached drawing, in which.

DESCRIPTION OF THE INVENTION

As embodied and broadly described herein, the disclosures herein provide detailed embodiments of the invention. However, the disclosed embodiments are merely exemplary of the invention that may be embodied in various and alternative forms. Therefore, there is no intent that specific structural and functional details should be limiting, but rather the intention is that they provide a basis for the claims and as a representative basis for teaching one skilled in the art to variously employ the present invention A problem in the art capable of being solved by the embodiments of the present invention is to provide a sensory feedback system worn by an individual. While the invention is describe as being used by a visually impaired or blind person, the invention can be used by a sighted person. When used by a sighted person, the invention may provide the person with additional information to enhance the person's understanding of what the person is seeing. For example, the invention may be used by sited people in low light environments, in medical situations, in industrial settings, or in other environments. Preferably, the device scans an area in the vicinity of the user and converts distance and location data of the objects scanned into audio signals.

Figure 1:
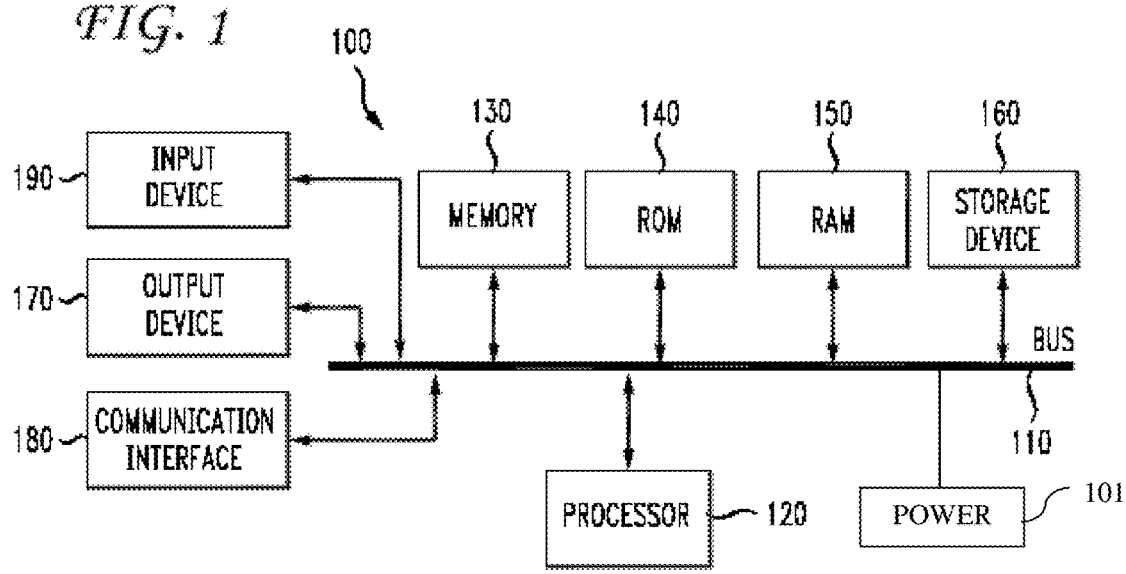
FIG. 1 a schematic of a preferred embodiment of a computing device.

FIG. 1 depicts a schematic of a preferred embodiment of a computing device 100 of the current invention. Device 100 preferably includes a power source 101. For example, power source 101 may be a battery, a chemical power source, a solar energy converter, a power converter to receive power from a wall receptacle or the like, a mechanical power source, or source of power.

Power source 101 is preferably used to supply power to the remaining components of computing device 100. Computing device 100 preferably further includes an integrated circuit (i.e. a system on a chip (SoC)). The SoC preferably integrates multiple components of a computer or other electronic system into a single chip. It may contain digital, analog, mixed-signal, and radio-frequency functions all on a single chip substrate. The SoC preferably incorporates one or more of a central processing unit (CPU), a graphics processing unit (GPU), and a system bus that couples various system components including the system memory, dynamic random access memory (RAM) 150 and flash memory 160, to the SoC. The system bus may be one of several types of bus structures including a memory bus or memory controller, a peripheral bus, or a local bus using one of a variety of bus architectures. A basic input/output (BIOS) stored in flash memory 160 or the like, may provide the basic routine that helps to transfer information between elements within computing device 100, such as during start-up. The drives and the associated computer readable media provide nonvolatile storage of computer readable instructions, data structures, program modules and other data for computing device 100. The basic components are known to those of skill in the art and appropriate variations are contemplated.

Although the exemplary environment described herein employs flash memory, it is appreciated by those skilled in the art that other types of computer readable media which can store data that are accessible by a computer, such as magnetic cassettes, hard drives, digital versatile disks, cartridges, random access memories (RAMs), read only memory (ROM), a cable or wireless signal containing a bit stream and the like, may also be used in the exemplary operating environment.

Computing device 100 further preferably includes a networking device 180. Networking device 180 is able to connect to, for example, the Internet, one or more Local Area Networks ("LANs"), one or more Metropolitan Area Networks ("MANs"), one or more Wide Area Networks ("WANs"), one or more Intranets, etc. Preferably networking device 105 is a Bluetooth device, however other networking devices can be used. Networking device 105 may be capable of connecting to wireless Bluetooth devices (e.g. a keyboard or a mouse). Preferably, networking device 180 is a wireless networking device (e.g. Wi-Fi), however hard-wired networks can be coupled to networking device 106 (e.g. ethernet). Furthermore, networking device 180 may also connect to distributed computing environments where tasks are performed by local and remote processing devices that are linked (either by hardwired links, wireless links, or by a combination thereof) through a communications network. In a distributed computing environment, program modules may be located in both local and remote memory storage devices.

To enable user interaction with computing device 100, there is preferably an input receiving device 190. Input receiving device 190 can receive input from a number of input mechanisms, such as a microphone for speech, a touch-sensitive screen for gesture or graphical input, a keyboard, a mouse, motion input, RJ-45, USB, and so forth. In some instances, multimodal systems enable a user to provide multiple types of input to communicate with the computing device 100. There is no restriction on the invention operating on any particular hardware arrangement and therefore the basic features here may easily be substituted for improved hardware or firmware arrangements as they are developed.

Computing device 100 further preferably includes at least one output port 170. Output port 170 connects computing device 100 to a TV, speaker, projector, or other audio visual device. Preferably, output port 1770 is a HDMI port, optical audio port, serial port, USB port, networking port, s-video port, coaxial cable port, composite video, composite audio, and/or VGA port. In preferred embodiments, computing device 100 may also include additional auxiliary components (e.g. power management devices or digital audio convertors).

For clarity of explanation, the illustrative system embodiments are presented as comprising individual functional blocks. The functions these blocks represent may be provided through the use of either shared or dedicated hardware, including, but not limited to, hardware capable of executing software. For example, the functions of one or more processors presented in FIG. 1 may be provided by a single shared processor or multiple processors. (Use of the term "processor" should not be construed to refer exclusively to hardware capable of executing software.) Illustrative embodiments may comprise microprocessor and/or digital signal processor (DSP) hardware, read-only memory (ROM) for storing software performing the operations discussed below, and random access memory (RAM) for storing results. Very large-scale integration (VLSI) hardware embodiments, as well as custom VLSI circuitry in combination with a general purpose DSP circuit, may also be provided.

Embodiments within the scope of the present invention include computer-readable media for carrying or having computer-executable instructions or data structures stored thereon. Such computer-readable media can be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium which can be used to carry or store desired program code means in the form of computer-executable instructions or data structures. When information is transferred or provided over a network or another communications connection (either hardwired, wireless, or combination thereof) to a computer, the computer properly views the connection as a computer-readable medium. Thus, any such connection is properly termed a computer-readable medium. Combinations of the above should also be included within the scope of the computer-readable media.

Computer-executable instructions include, for example, instructions and data which cause a computer, specialty computer, or special purpose processing device to perform a certain function or group of functions. Computer-executable instructions also include program modules that are executed by computers in stand-alone or network environments. Generally, program modules include routines, programs, objects, components, and data structures, etc. that perform particular tasks or implement particular abstract data types. Computer-executable instructions, associated data structures, and program modules represent examples of the program code means for executing steps of the methods disclosed herein. The particular sequence of such executable instructions or associated data structures represents examples of corresponding acts for implementing the functions described in such steps.

Figure 2:
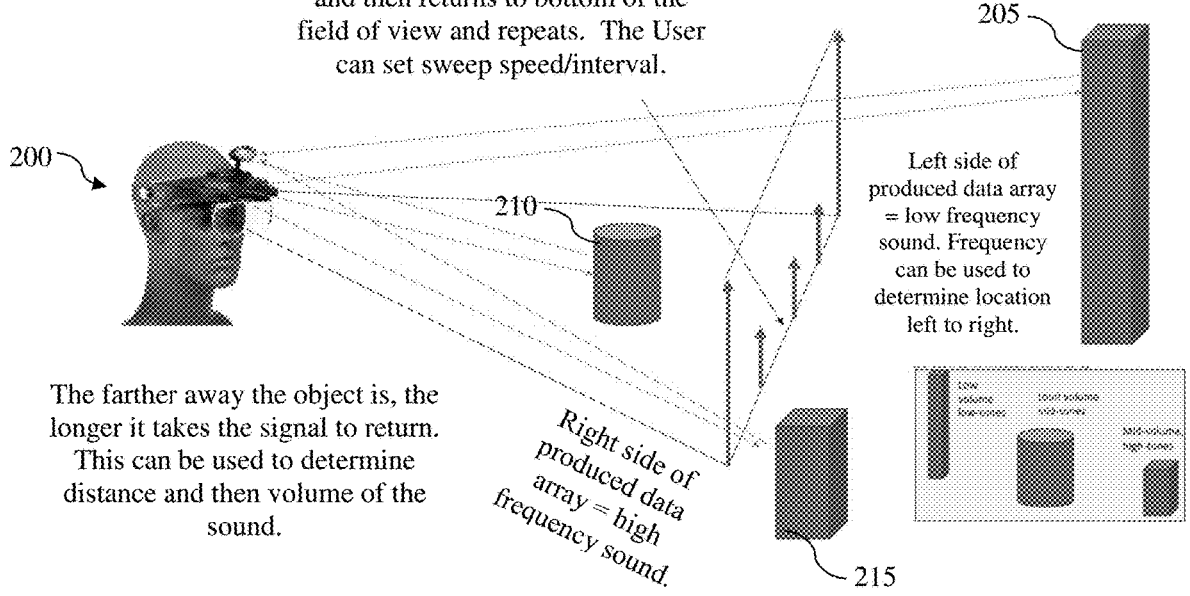
FIG. 2 depicts a diagram of the system of the invention in use.

FIG. 2 depicts an embodiment of device 200 in use. Preferably device 200 is a head wearable device that includes a signal transmitter and a signal receiver. In other embodiments, device 200 may be handheld, worn on another portion of the user, or be a standalone device. Device 200 preferably has one or more sound producing devices. The sound producing devices may be, for example headphones, earbuds, or speakers. Device 200 may be one unit or multiple units. Device 200 may have internal processing capabilities or use the processing capabilities of another user device (i.e. a smartphone, a tablet, a computer, or another dedicated device).

In the preferred embodiment, device 200 is able to discern the direction the user is facing. For example, in the head worn embodiment, the device will preferably point in the direction the user is facing. In other embodiments, device 200 may use geolocating technology (i.e. GPS or cellular triangulation) and/or accelerometers to determine the user's position. Device 200 may also be able to detect if the user is moving (including but not limited to the direction, speed, and acceleration), the user's head and/or body position (i.e. head tilt, facing up, facing down, or other head orientation), the elevation of device 200, and/or other position information.

In a preferred embodiment, device 200 emits a signal via one or more signal transmitters. The signal is preferably an electromagnetic wave sent out from device 200. For example, the signal may be a Radar (i.e. low frequency) electromagnetic wave, a LiDAR (i.e. high frequency) electromagnetic wave, or a visible light. In other embodiments, the signal may be a sound wave (i.e. Sonar) or another emission or combinations thereof. Each signal preferably reflects off surfaces and returns to device 200. One or more signal receivers preferably detect the reflected signal and, based on the amount of time the signal took to return, device 200 is able to determine the distance of the surface. The device may also emit different frequencies and use the reflected signal to determine properties of objects in the field of view of the device. For example, to see what is under ice, ground penetrating radar frequencies may be used (different frequencies penetrate different depths). The system may use different emissions to determine color of objects, density, etc. In these cases, the data array would not represent distance, but rather another variable. A user may be able to switch between, distance, color, density, etc. In other embodiments the different data types may be layered and sonified. Preferably, device 200 transmits multiple signals to sweep (both side to side and up and down) to get multiple data points for the field of view. The field of view may be 360° around the user, 180° in front of the user, or a smaller or larger filed of view. Depending on the fidelity desired, more or fewer signals may be emitted and received.

While the invention is describe as obtaining an image using a wearable or hand held image capture device, the image capture device may be a stationary image capture device, a vehicle mounted image capture device, a portable image capture device, or another device capable of obtaining an image. For example, the device may be a telescope, a scanner, a microscope, a webcam, a camera, a satellite, a video camera, a medical imaging device (i.e. a CT Scanner, an MRI, or an X-Ray machine), or another image capturing device. While the device is described as capturing visual data, the device may capture non-visual data. For example, the device may capture infrared data, ultra-violet data, x-ray data, gamma ray data, or other data in the light spectrum. In some embodiments, the image data may be obtained from non-image capturing sources. For example, the image may be a computer generated image. Preferably, device 200 is adapted to convert any digital image (still or video) into a sonification.

In the preferred embodiment, once the signals are received, device 200 compiles the data into an array of data points (or pixels). The data points preferably indicate the horizontal position (i.e., x-axis), elevation (i.e., y-axis), and distance or other property (i.e., z-axis) of detected objects. The compiled data points create a 3-D sonification of the field of view. The 3-D sonification is then transmitted to the user via the sound producing devices. For example, data points from the left side of the field of view are transmitted at lower frequencies or tones, data point from the middle of the field of view are transmitted a middle frequencies or tones, and data points from the right side of the field of view are transmitted at higher frequencies or tones (or vice versa). Data points from closer objects preferably are transmitted at higher volumes and data points from further objects are transmitted at lower volumes. To transmit the elevation of the datapoints, preferably slices of the 3-D sonification are transmitted in sequence over time. For example, starting with the data points at the bottom of the field of view, a first sound transmission will be emitted. Then sweeping up the field of view, subsequent sound transmissions will be emitted in sequence until the entire 3-D sonification has been emitted. While, frequency is described as indicating the left-right information, volume is described as indicating the distance information, and time is described as indicating the elevation information, frequency, volume, and/or time can indicate different information within the dataset. Additionally, the information can be presented in other forms. For example, the amount of sound emitted from one headphone versus the other headphone may be used to provide information.

Preferably, the entire 3-D sonification is emitted in less than 5 seconds, preferably less than 2 seconds, or more preferably 1 second or less. The time frame may be adjustable by the user. Depending on the number of data points and the fidelity of the 3-D sonification, more or fewer slices of the 3-D sonification will be emitted. Additionally, as the user moves, the 3-D sonification is preferably updated, in real- or near real-time, to provide the user with changes in the environment.

For example, as shown in FIG. 2, object 205 may be sonified as a low volume and a low tone, object 210 may be sonified as a high volume and a middle tone, and object 215 may be sonified as middle volume and high tone. Furthermore, as indicated in box 220, the sonification indicating object 215 may begin in the beginning of the sound sweep and end in the middle of the sound sweep, indicating that object 215 is short and on the ground. The sonification indicating object 210 may begin in the middle of the sound sweep and end later in the middle of the sound sweep, indicating that object 210 is floating in the middle of the field of view. The sonification indicating object 205 may begin in the middle of the sound sweep and end at the end of the sound sweep, indicating that object 205 is floating at the top of the field of view.

Figure 3A:
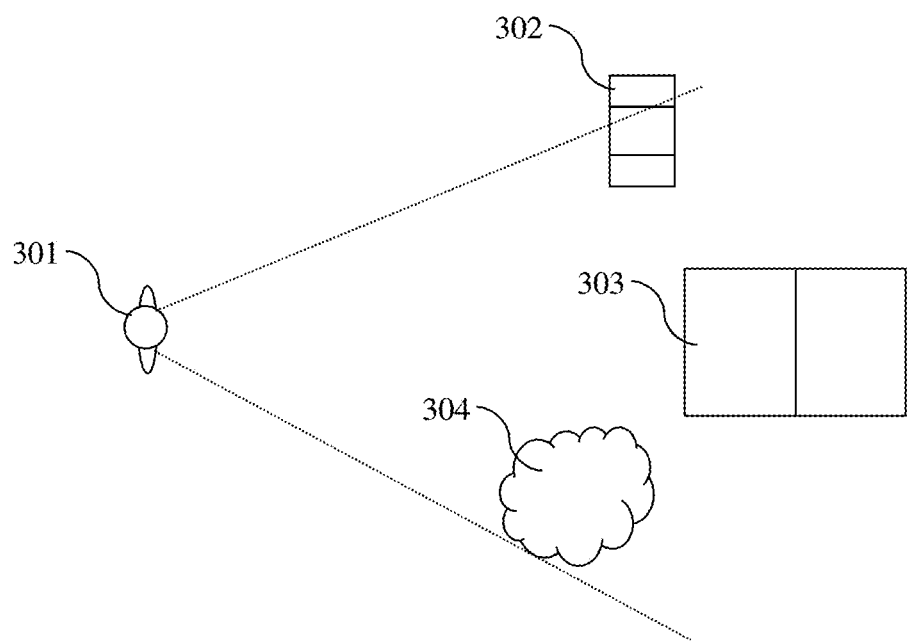
FIGS. 3A-B depict another embodiment of the invention in use.
Figure 3B:

FIG. 3A depicts an embodiment of a user's field of view. In the figure, the user 301 is facing a car (in the middle distance) 302, a house (in the far distance) 303, and a tree (near user 301) 304. In the example, a portion of the car is outside the user's field of view. As described herein, device 200 scans the scene and compiles reflected signals into an array of data points (or pixels). FIG. 3B depicts the array of data points (for simplicity, the fidelity of the array is very low with few data points, preferably there will be hundreds or thousands of data points depending on the desired fidelity, processing power, and other traits of device 200). With this array of data points, device 200 preferably has an elevation (A-G), a horizontal position (1-8), and a distance for each object within the field of view.

Device 200, beginning at row A, will preferably emit a chord of sound for each row. For example, since each pixel except A6 and A8 contain an object, the sound frequencies associated with the remaining pixels will be played. Additionally, the sound frequencies associated with the tree will be loudest, the sound frequencies associated with the car will have a middle volume, and the sound frequencies associated with the house will be the softest (based on their distances in FIG. 3A). Device 200 will preferably, in sequence, play the chord for each remaining row, B to G, until the 3-D sonification for the entire scene has been played. As only the tree is tall enough to reach row G, only the sound frequencies associated with the position of the tree will be played for row G. While the embodiment is described as sweeping up the field of view, it may also sweep down the field of view.

Figure 4:
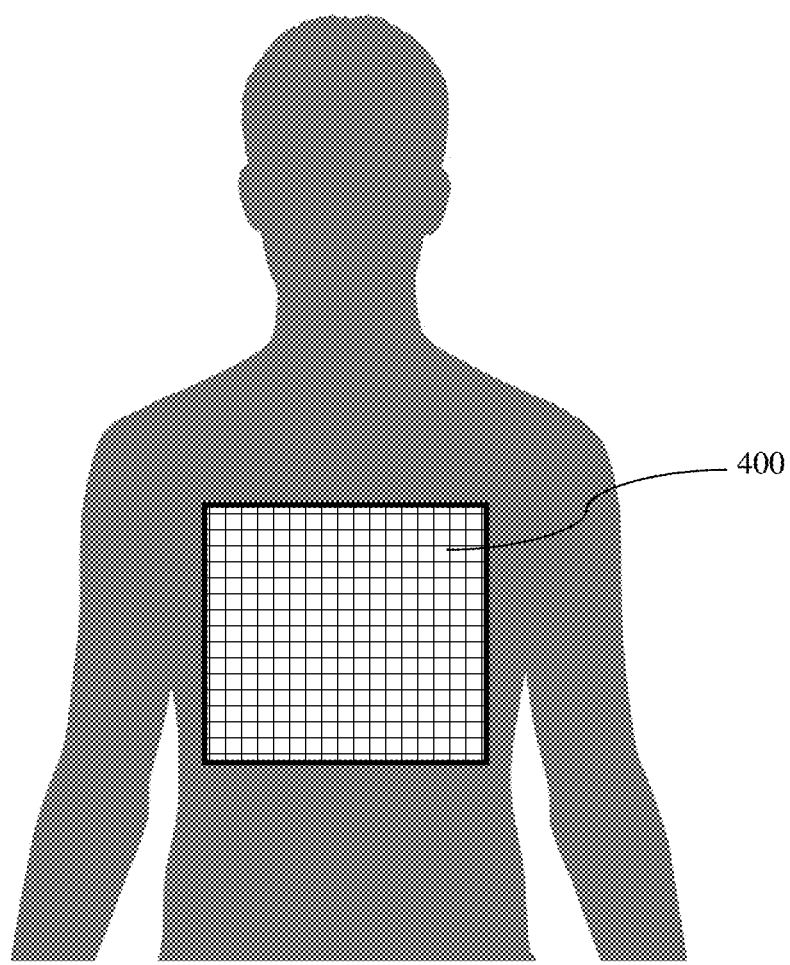
FIG. 4 depicts an embodiment of the invention using a tactile device.

FIG. 4 depicts a wearable tactile device 400. Device 400 is preferably warn against a user's skin. Device 400 can be used instead of the audible output of device 200 or in conjunction with the audible output of device 200. Device 400 preferably is adapted to convert the image created from a scan of the field of view in front of the user into a haptic output. Preferably, device 400 has rows of cells that are able to be extended and retracted to create a haptic image. For example, the top row of cells may correspond to the top of the field of view, and the bottom row of cells may correspond to the bottom of the field of view, etc. Each pixel in the array worn by the user preferably has a unique haptic response. In a preferred embodiment, the stronger the response/vibration, the closer the object is. Additionally, each cell may be able to extend to multiple depths. A second device could be worn on a user's back providing forward view as well as rear view.

Other embodiments and uses of the invention will be apparent to those skilled in the art from consideration of the specification and practice of the invention disclosed herein. All references cited herein, including all publications, U.S. and foreign patents and patent applications, are specifically and entirely incorporated by reference. It is intended that the specification and examples be considered exemplary only with the true scope and spirit of the invention indicated by the following claims. Furthermore, the term "comprising of" includes the terms "consisting of" and "consisting essentially of."

The invention claimed is:

1. A system of presenting environmental data, comprising:
   a frequency emitting device;
   a frequency receiving device, wherein the frequency receiving device is tuned to receive a reflected signal from the frequency emitting device;
   a processor, wherein the processor is programmed to:
      compile data from the reflected signal; and
      convert the data from the reflected signal into a sound transmission, wherein the sound transmission comprises a data array having a distance component, a horizontal position component, and a vertical position component corresponding to the data of the reflected signal; and
   a sound emitting device adapted to play the sound transmission.

2. The system of claim 1, wherein the frequency emitting device emits a plurality of signals directed toward at least a portion of the environment, the frequency receiving device is adapted to receive reflections from the plurality of signals, and the processor is adapted to differentiate between each sent and received signal and compile an array of data based on the received signals.

3. The system of claim 2, wherein the processor converts the array of data into a sonification of the environment.

4. The system of claim 3, wherein the sonification of the environment is a three-dimensional representation of the environment.

5. The system of claim 4, wherein a tone of the sonification represents the horizontal position of a reflected signal, a volume of the sonification indicates a property of the reflected signal, and a length of the sonification represents a vertical position of the reflected signal.

6. The system of claim 5, wherein the property is at least one of distance information, color information, density information, or combinations thereof.

7. The system of claim 1, wherein the frequency emitting device and the frequency receiving device is one of a LIDAR system, a RADAR system, or a SONAR system.

8. The system of claim 1, wherein at least a portion of the system is wearable.

9. The system of claim 1, wherein the frequency emitting device and the frequency receiving device continuously sweep the environment to update the data compiled by the processor and the sound transmission.

10. The system of claim 9, wherein the sound emitting device repeatedly emits the sound transmission as the processor updates the sound transmission.

11. The system of claim 1, further comprising a haptic information delivery device.

12. A method of presenting environmental data, comprising the steps of:
emitting at least one frequency from a frequency emitting device;
receiving a reflection of the at least one emitted frequency on a frequency receiving device;
compiling data from the reflected signal on a processor;
converting the data from the reflected signal into a sound transmission on the processor,
wherein the sound transmission comprises a data array having a distance component, a horizontal position component, and a vertical position component corresponding to the data of the reflected signal; and
playing the sound transmission on a sound emitting device.

13. The method of claim 12, further comprising delivering data through a haptic information delivery device.

14. The method of claim 12, wherein the frequency emitting device emits a plurality of signals directed toward at least a portion of the environment, the frequency receiving device is adapted to receive reflections from the plurality of signals, and the processor is adapted to differentiate between each sent and received signal and compile an array of data based on the received signals.

15. The method of claim 14, further comprising converting the array of data into a sonification of the environment on the processor.

16. The method of claim 15, wherein the sonification of the environment is a three-dimensional representation of the environment.

17. The method of claim 16, wherein a tone of the sonification represents the horizontal position of a reflected signal, a volume of the sonification indicates a property of the reflected signal, and a length of the sonification represents a vertical position of the reflected signal.

18. The method of claim 17, wherein the property is at least one of distance information, color information, density information, or combinations thereof.

19. The method of claim 13, wherein the frequency emitting device and the frequency receiving device is one of a LIDAR system, a RADAR system, or a SONAR system.

20. The method of claim 13, wherein the frequency emitting device and the frequency receiving device continuously sweep the environment to update the data compiled by the processor and the sound transmission.

21. The method of claim 20, wherein the sound emitting device repeatedly emits the sound transmission as the processor updates the sound transmission.

22. The method of claim 13, further comprising detecting a direction of a field of view of a user.

* * * * *